US012738077B2

(12) United States Patent
Bugay et al.

(10) Patent No.: US 12,738,077 B2
(45) Date of Patent: Sep. 15, 2026

(54) METHODS, SYSTEMS, AND COMPUTER PROGRAM PRODUCT FOR REMOVING EXTRANEOUS CONTENT FROM DRUG PRODUCT PACKAGING TO FACILITATE VALIDATION OF THE CONTENTS THEREIN

(71) Applicant: PARATA SYSTEMS, LLC, Durham, NC (US)

(72) Inventors: John Alfred Bugay, Eden, UT (US); Todd Martin Jenkins, Raleigh, NC (US); Russell F. Lewis, Dallas, TX (US); Corey Spencer Martin, Raleigh, NC (US); Abhishek Ray, New Town (IN); Arthur F. Swanson, Cary, NC (US); Rongkai Xu, Morganville, NJ (US)

(73) Assignee: PARATA SYSTEMS, LLC, Durham, NC (US)

(*) Notice: Subject to any disclaimer, the term of this patent is extended or adjusted under 35 U.S.C. 154(b) by 649 days.

(21) Appl. No.: 17/649,208

(22) Filed: Jan. 28, 2022

(65) Prior Publication Data

US 2022/0254172 A1 Aug. 11, 2022

Related U.S. Application Data

(60) Provisional application No. 63/143,400, filed on Jan. 29, 2021.

(51) Int. Cl.

*G06V 20/62* (2022.01)
*G06T 5/70* (2024.01)

(Continued)

(52) U.S. Cl.

CPC ................ *G06V 20/62* (2022.01); *G06T 5/70* (2024.01); *G06V 10/82* (2022.01); *G16H 70/40* (2018.01); *G06T 2207/20084* (2013.01)

(58) Field of Classification Search

CPC ........ G06V 20/62; G06V 10/82; G16H 70/40; G06T 5/70; G06T 2207/20084

See application file for complete search history.

(56) References Cited

U.S. PATENT DOCUMENTS 8,712,163 B1 4/2014 Osheroff
8,943,779 B2 2/2015 Amano et al.

(Continued)

FOREIGN PATENT DOCUMENTS

CN 107958250 A 4/2018
JP H0599861 A 4/1993

(Continued)

OTHER PUBLICATIONS

International Search Report and Written Opinion corresponding to PCT/US2022/014251; mailed May 4, 2022 (9 pages).

(Continued)

*Primary Examiner* — John J Lee
(74) *Attorney, Agent, or Firm* — Myers Bigel, P.A.

(57) ABSTRACT

A method includes receiving an image of a drug product package that contains one or more drug products therein, the image including labeling content displayed on a surface thereof; detecting, using an artificial intelligence engine, the labeling content on the surface of the drug product package; and generating a modified image of the drug product package that has the labeling content removed from surface thereof.

20 Claims, 11 Drawing Sheets

(51) Int. Cl.
*G06V 10/82* (2022.01)
*G16H 70/40* (2018.01)

(56) References Cited

U.S. PATENT DOCUMENTS

| | | | | |
|---|---|---|---|---|
| 9,870,611 | B2 | 1/2018 | Ito et al. | |
| 10,593,425 | B1 | 3/2020 | Truscott et al. | |
| 10,892,048 | B2 | 1/2021 | Reddy et al. | |
| 2005/0027664 | A1 * | 2/2005 | Johnson | G06F 40/45 706/12 |
| 2013/0058550 | A1 | 3/2013 | Tanimoto et al. | |
| 2016/0055317 | A1 * | 2/2016 | Levine | G06K 7/10297 705/2 |
| 2020/0085685 | A1 * | 3/2020 | Blalock | B65D 83/04 |

FOREIGN PATENT DOCUMENTS

| | | | | |
|---|---|---|---|---|
| KR | 200464617 | Y1 * | 1/2013 | G09F 3/02 |
| KR | 20170054529 | A | 5/2017 | |
| KR | 101744123 | B1 | 6/2017 | |

OTHER PUBLICATIONS

Extended European Search Report corresponding to EP 22746666.1; dated Nov. 15, 2024, (10 pages).
Chung, Sheng-Luen , et al., "End-to-end identification of pharmaceutical blister packages based on one-side handheld images", 2020 International Conference on System Science and Engineering (ICSSE), Kagawa, Japan, 1-5.
Liu, Xuebo , et al., "FOTS: Fast Oriented Text Spotting With a Unified Network", Proceedings of the IEEE Conference on Computer Vision and Pattern Recognition (CVPR), 2018, 5676-5685.
Australian Examination Report No. 1 corresponding to AU2022214915; dated Mar. 20, 2024, (7 pages).
Liu, et al., "DLI-IT: a deep learning approach to drug label identification through image and text embedding", BMC Medical Informatics and Decision Making, 20:68, 2020, (9 pages).
First Korean Office Action issued in corresponding KR 10-2023-7027805, on Feb. 23, 2026. English translation included, (8 pages).
First Chinese Office Action (including English translation) corresponding to CN 202280012116.X; Date: Aug. 23, 2025, (12 pp).

* cited by examiner

METHODS, SYSTEMS, AND COMPUTER PROGRAM PRODUCT FOR REMOVING EXTRANEOUS CONTENT FROM DRUG PRODUCT PACKAGING TO FACILITATE VALIDATION OF THE CONTENTS THEREIN

RELATED APPLICATION

The present application claims priority from and the benefit of U.S. Provisional Application No. 63/143,400, filed Jan. 29, 2021, the disclosure of which is hereby incorporated herein by reference in its entirety.

BACKGROUND

The present disclosure relates generally to the packaging of drug products, and, in particular, to methods, systems, and computer program products for removing extraneous content from a surface drug product package to facilitate validation of the drug product package contents.

Drug product packaging systems may be used in facilities, such as pharmacies, hospitals, long term care facilities, and the like to dispense medications to fill prescriptions. These drug product packaging systems may include systems designed to package medications in various container types including, but not limited to, pouches, vials, bottles, blistercard, and strip packaging. Strip packaging is a type of packaging wherein medications are packaged in individual pouches for administration on a specific date and, in some cases, at a specific time. Typically, individual pouches are removably joined together and often provided in rolls. The pouches can be separated from the roll when needed.

Some types of drug product packages, such as pouches and blistercards, for example, may contain content printed thereon, such as Personal Health Information (PHI), manufacturer information, e.g., logos, names, contact information, etc., and/or other details about the content of the drug product package, such as number of drug products, drug product names, dosing times, dosing strengths, barcodes, and the like. Such content on the surface of the drug product package may make it more difficult to validate the content of the drug product package through imaging of the drug product package.

SUMMARY

In some embodiments of the inventive concept, a method comprises, receiving an image of a drug product package that contains one or more drug products therein, the image including labeling content displayed on a surface thereof; detecting, using an artificial intelligence engine, the labeling content on the surface of the drug product package; and generating a modified image of the drug product package that has the labeling content removed from surface thereof.

In other embodiments, the labeling content comprises commercial marketing information, patient identification information, or personal healthcare information.

In still other embodiments, the commercial marketing information comprises a logo or a business name; the patient identification information comprises a patient name, a patient phone number, a patient address, or a patient identification number; and the personal healthcare information comprises names of the one or more drug products, a number of each of the one or more drug products, a prescribed time of administration for each of the one or more drug products, or one or more barcodes associated with the one or more drug products, a prescription order, a patient account, an identification number, or other information.

In still other embodiments, the method further comprises performing gamma correction on the image of the drug product package responsive to receiving the image of the drug product package to generate a gamma corrected image of the drug product package; performing gaussian blur denoising on the gamma corrected image of the drug product package to generate a reduced noise image of the drug product package; and performing automatic image thresholding on the reduced noise image of the drug product package to generate a foreground-background separated image of the drug product package. Detecting, using the artificial intelligence engine, the labeling content comprises detecting, using the artificial intelligence engine, the labeling content on the surface of the foreground-background separated image of the drug product package.

In still other embodiments, the artificial intelligence engine is a convolutional neural network.

In still other embodiments, the convolutional neural network comprises a plurality of convolutional layers with at least some of the plurality of convolutional layers being connected to one another via a skip connection.

In still other embodiments, the artificial intelligence engine is a first artificial intelligence engine and the modified image is a first modified image. The method further comprises: receiving order information for the one or more drug products and an identifier for the drug product package; detecting, using a second artificial intelligence engine, individual ones of the one or more drug products in the first modified image; and generating a second modified image of the drug product package that includes indicia that distinguish between the individual ones of the one or more drug products and associate the one or more drug products with the order information and the identifier for the drug product package.

In still other embodiments, the indicia that distinguish between the individual ones of the one or more drug products comprise one or more bounding boxes.

In still other embodiments, the order information comprises names for the one or more drug products in the drug product package. The method further comprises identifying, using a third artificial intelligence engine, at least some of the one or more drug products in the second modified image based on the names for the one or more drug products. The names are associated with drug product attributes in a reference database In still other embodiments, the at least some of the one or more drug products includes a fragmented one of the one or more drug products.

In still other embodiments, the method further comprises identifying, using the third artificial intelligence engine, a portion of the one or more drug products as debris resulting from damage to the one or more drug products.

In still other embodiments, the method further comprises annotating the at least some of the one or more drug products in the second modified image with the names for the one or more drug products.

In still other embodiments, the method further comprises annotating any of the one or more drug products that have not been annotated with the names with an unknown drug product label.

In still other embodiments, the names are first names and the order information comprises National Drug Codes (NDCs) for the one or more drug products in the drug product package. The method further comprises: matching NDCs that are not associated with the at least some of the one or more drug products that have been annotated with the first names with drug product reference data; and annotating any of the one or more drug products that have not been annotated with the names that have associated NDCs that match with the drug product reference data with second names based on drug product reference data.

In still other embodiments, the drug product reference data comprise a drug product shape, a drug product color, a drug product etching, drug product imprint, a drug product weight, and/or a drug product label.

In some embodiments of the inventive concept, a system comprises a processor; and a memory coupled to the processor and comprising computer readable program code embodied in the memory that is executable by the processor to perform operations comprising: receiving an image of a drug product package that contains one or more drug products therein, the image including labeling content displayed on a surface thereof; detecting, using an artificial intelligence engine, the labeling content on the surface of the drug product package; and generating a modified image of the drug product package that has the labeling content removed from surface thereof.

In further embodiments, the operations further comprise: performing gamma correction on the image of the drug product package responsive to receiving the image of the drug product package to generate a gamma corrected image of the drug product package; performing gaussian blur denoising on the gamma corrected image of the drug product package to generate a reduced noise image of the drug product package; and performing automatic image thresholding on the reduced noise image of the drug product package to generate a foreground-background separated image of the drug product package. Detecting, using the artificial intelligence engine, the labeling content comprises detecting, using the artificial intelligence engine, the labeling content on the surface of the foreground-background separated image of the drug product package.

In still further embodiments, the artificial intelligence engine is a convolutional neural network.

In some embodiments of the inventive concept, a computer program product comprises a non-transitory computer readable storage medium comprising computer readable program code embodied in the medium that is executable by a processor to perform operations comprising: receiving an image of a drug product package that contains one or more drug products therein, the image including labeling content displayed on a surface thereof; detecting, using an artificial intelligence engine, the labeling content on the surface of the drug product package; and generating a modified image of the drug product package that has the labeling content removed from surface thereof.

In other embodiments, the operations further comprise: performing gamma correction on the image of the drug product package responsive to receiving the image of the drug product package to generate a gamma corrected image of the drug product package; performing gaussian blur denoising on the gamma corrected image of the drug product package to generate a reduced noise image of the drug product package; and performing automatic image thresholding on the reduced noise image of the drug product package to generate a foreground-background separated image of the drug product package. Detecting, using the artificial intelligence engine, the labeling content comprises detecting, using the artificial intelligence engine, the labeling content on the surface of the foreground-background separated image of the drug product package.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter, and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
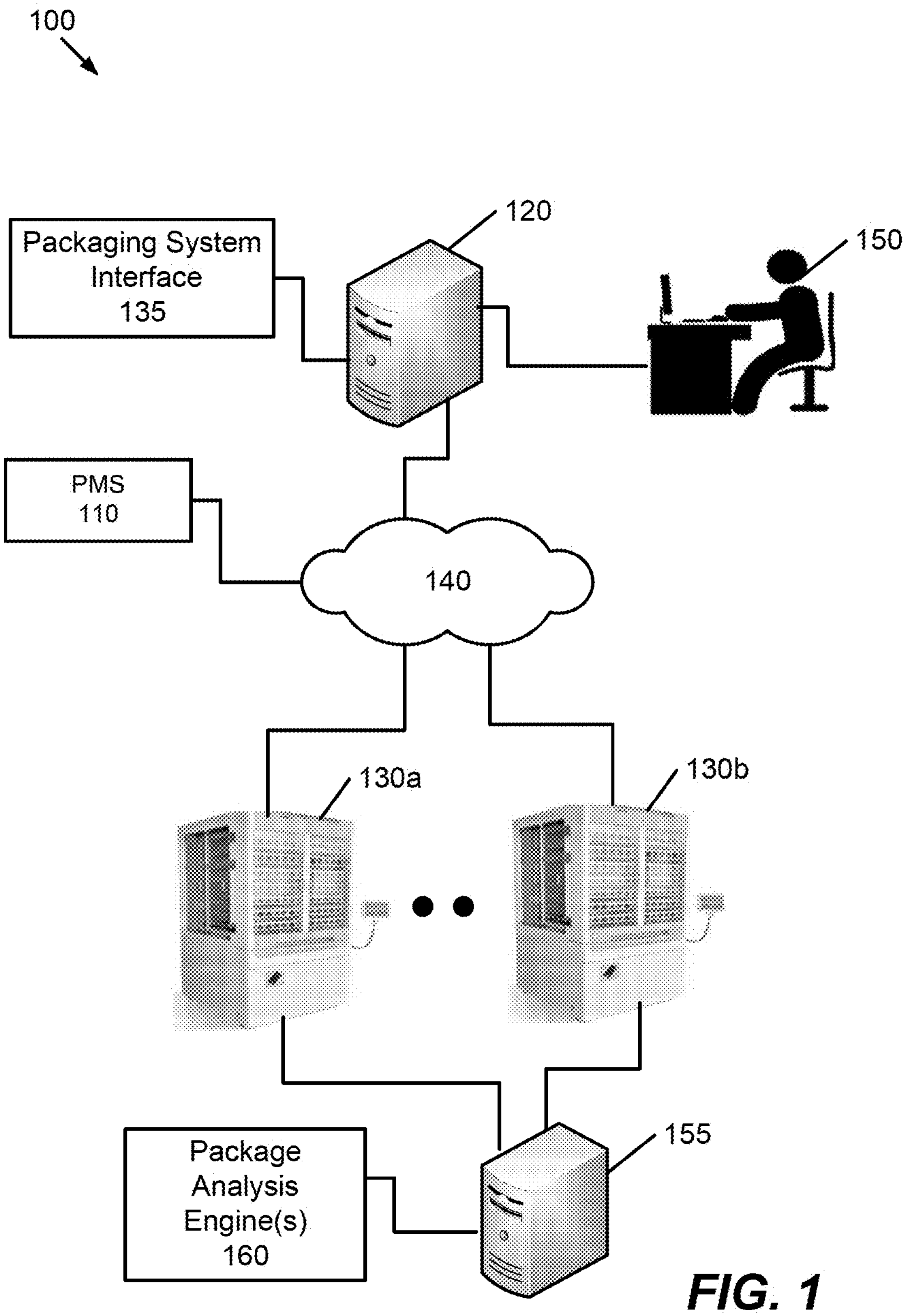
FIG. 1 is a block diagram that illustrates a communication network including an Artificial Intelligence (AI) assisted drug product package analysis system in accordance with some embodiments of the inventive concept.

In the following detailed description, numerous specific details are set forth to provide a thorough understanding of embodiments of the present inventive concept. However, it will be understood by those skilled in the art that the present invention may be practiced without these specific details. In some instances, well-known methods, procedures, components and circuits have not been described in detail so as not to obscure the present inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "data processing facility" includes, but it is not limited to, a hardware element, firmware component, and/or software component. A data processing system may be configured with one or more data processing facilities.

The term "drug product packaging system," as used herein, refers to any type of pharmaceutical dispensing system including, but not limited to, automated systems that fill vials, bottles, containers, pouches, blistercards, or the like with drug product, semi-automated systems that fill vials, bottles, containers, pouches, blistercards, or the like with drug product, and any combination of automated and semi-automated systems for filling a drug product package with drug product. Drug product packaging system also includes packaging systems for pharmaceutical alternatives, such as nutraceuticals and/or bioceuticals.

The terms "pharmaceutical" and "medication," as used herein, are interchangeable and refer to medicaments prescribed to patients either human or animal. A pharmaceutical or medication may be embodied in a variety of ways including, but not limited to, pill form capsule form, tablet form, and the like.

The term "drug product" refers to any type of medicament that can be packaged within a vial, bottle, container, pouch, blistercard, or the like by automated and semi-automated drug product packaging systems including, but not limited to, pills, capsules, tablets, caplets, gel caps, lozenges, and the like. Drug product also refers to pharmaceutical alternatives, such as nutraceuticals and/or bioceuticals. Example drug product packaging systems including management techniques for fulfilling packaging orders are described in U.S. Pat. No. 10,492,987 the disclosure of which is hereby incorporated herein by reference.

The term "drug product package" refers to any type of object that can hold a drug product including, but not limited to, a vial, bottle, container, pouch, blistercard, or the like.

Embodiments of the inventive concept are described herein in the context of a drug product packaging analysis engine that includes one or more machine learning engines and artificial intelligence (AI) engines. It will be understood that embodiments of the inventive concept are not limited to particular implementations of the drug product analysis engine and various types of AI systems may be used including, but not limited to, a multi-layer neural network, a deep learning system, a natural language processing system, and/or computer vision system Moreover, it will be understood that the multi-layer neural network is a multi-layer artificial neural network comprising artificial neurons or nodes and does not include a biological neural network comprising real biological neurons. Embodiments of the inventive concept may be implemented using multiple AI systems or may be implemented by combining various functionalities into fewer or a single AI system.

Some embodiments of the inventive concept stem from a realization that when validating the contents of a drug product package, such as a pouch or blistercard, for example, labeling content on the surface of the drug product package may obscure the drug products contained therein when performing an image analysis of the drug product package. Embodiments of the inventive concept provide an AI assisted drug product package analysis system that may use an AI engine to detect the labeling content on the surface of a drug product package and may generated a modified image of the drug product package with the labeling content removed. The labeling content may include, for example, commercial marketing information, patient identification information, personal healthcare information (PHI), and the like. With the labeling content removed from the surface of the drug product package, an AI system may be used to detect one or more individual ones of the drug products contained in the package and a second modified image may be generated that includes indicia, such as boundary boxes, that distinguish between individual ones of the drug products contained in the drug product package. In some embodiments, drug products that are fragmented or even damaged so as to be debris may be distinguished by the indicia. An AI system may then be used to identify one or more of the drug products contained in the drug product package with names of the particular drug products. In some embodiments, whole drug products, fragmented drug products, and/or debris may be identified by name using the AI system based on attributes of the drug products, e.g., shape, color, etching(s), imprint(s), weight, and/or label(s), along with knowledge of the drug product package contents and successful identification of other ones of the drug products contained in the drug product package. Unidentifiable drug products may be further analyzed through matching of National Drug Codes (NDCs) or Drug Identification Numbers (DINs) for drug products contained in the drug product package with drug product reference data, which may include drug product shape, color, etching(s), imprint(s), weight, and/or label(s) information. As used herein, NDC may be used to represent both NDC information and DIN information. Upon obtaining a match these drug products may be annotated with a name based on the drug product reference data and the NDC. Embodiments of the inventive concept may also be used for filling and validating unit of use packages (i.e., each package contains a single dose of a single drug product). Unit of use packages may be patient specific but also may be produced without patient information so that they can be used as floor stock in a hospital or long-term care facility, for example, for one time or emergency use. Each of those pouches (or blisters on a card) may have label information, that may be a subset or slightly different than typical prescription drug product packages. For example, a unit of use package may have drug product name, dosage, NDC, manufacturer, lot number, expiration date and/or beyond-use-date (BUD). The package may also include pharmacy information or information about the facility that the unit of use package is provided to.

Referring to FIG. 1, a communication network **100*a* including an AI assisted drug product package analysis system, in accordance with some embodiments of the inventive concept, comprises a pharmacy management system (PMS) or host system 110, a packaging system server 120, a package analysis engine(s) server 155, and one or more drug product packaging systems 130*a* and 130*b* that are coupled via a network 140** as shown.

The PMS system 110 may be configured to manage and fill prescriptions for customers. As used herein, PMS systems may be used in pharmacies or may be used generally as batch-generating systems for other applications, such as dispensing nutraceuticals or bioceuticals. The PMS system 110 may be associated with a variety of types of facilities, such as pharmacies, hospitals, long term care facilities, and the like. The PMS system or host system 110 may be any system capable of sending a valid prescription to the one or more product packaging systems **130*a* and 130*b*. The packaging system server 120 may include a packaging system interface module 135 and may be configured to manage the operation of the drug product packaging systems 130*a*** and 130*b*. For example, the packaging system server 120 may be configured to receive packaging orders from the PMS system 110 and to identify which of the drug product packaging systems 130*a* and 130*b* should be used to package particular individual orders or batches of orders. In addition, the packaging system server 120 may be configured to manage the operations of the drug product packaging systems 130*a* and 130*b*. For example, the packaging system server 120 may be configured to manage the inventory of drug product available through each of the drug product packaging systems 130*a* and 130*b*, to manage the drug product dispensing canisters assigned or registered to one or more of the drug product packaging systems 130*a* and 130*b*, to manage the operational status generally of the drug product packaging systems 130*a* and 130*b*, and/or to manage reports regarding the status (e.g., assignment, completion, etc.) of packaging orders, drug product inventory, order billing, and the like. A user 150, such as a pharmacist or pharmacy technician, may communicate with the packaging system server 120 using any suitable computing device via a wired and/or wireless connection. Although the user 150 is shown communicating with the packaging system server 120 via a direct connection in FIG. 1, it will be understood that the user 150 may communicate with the packaging system server 120 via one or more network connections. The user 150 may interact with the packaging system server 120 to approve or override various recommendations made by the packaging system server 120 in operating the drug product packaging systems 130*a* and 130*b*. The user 150 may also initiate the running of various reports as described above for the drug product packaging systems 130*a* and 130*b*. Although only two drug product packaging systems 130*a* and 130*b* are shown in FIG. 1, it will be understood that more than two drug product packaging systems may be managed by the packaging system server 120.

The AI assisted drug product package analysis system may include the package analysis engine(s) server 155, which includes a package analysis engine(s) module 160 to facilitate validation of the contents of a drug product package by removing extraneous content from images of the drug product packaging. The package analysis engine(s) server 155 and package analysis engine(s) module 160 may represent one or more AI systems that may be configured to generate modified images of drug product packages with labeling content removed from one or more surfaces thereof, to detect in a drug product package image individual ones of one or more drug products contained in the drug product package, and/or to identify these drug products that have been detected in the drug product package image. In accordance with various embodiments of the inventive concept, the labeling content can be removed from any surface on the drug product package including multiple surfaces of the drug product package, such as the top, bottom, and sides of vials, front and back surfaces of pouches and blister packs, and the like.

It will be understood that the division of functionality described herein between the packaging system server 120/packaging system interface module 135 and the package analysis engine(s) server 155/package analysis engine(s) module 160 is an example. Various functionality and capabilities can be moved between the packaging system server 120/packaging system interface module 145 and the package analysis engine(s) server 155/package analysis engine(s) module 160 in accordance with different embodiments of the inventive concept. Moreover, in some embodiments, the packaging system server 120/packaging system interface module 135 and the package analysis engine(s) server 155/package analysis engine(s) module 160 may be merged as a single logical and/or physical entity.

A network 140 couples the drug product packaging systems 130*a* and 130*b*, the PMS system 110, and the packaging system server 120 to one another. The network 140 may be a global network, such as the Internet or other publicly accessible network. Various elements of the network 140 may be interconnected by a wide area network, a local area network, an Intranet, and/or other private network, which may not be accessible by the general public. Thus, the communication network 140 may represent a combination of public and private networks or a virtual private network (VPN). The network 140 may be a wireless network, a wireline network, or may be a combination of both wireless and wireline networks. In some embodiments, the package analysis engine(s) server 155 may also be coupled to the network 140.

The AI assisted drug product package analysis service provided through the package analysis engine(s) 155, and package analysis engine(s) module 160, in some embodiments, may be implemented as a cloud service. In some embodiments, the AI assisted drug product package analysis service may be implemented as a Representational State Transfer Web Service (RESTful Web service).

Although FIG. 1 illustrates an example communication network that includes AI assisted drug product package analysis systems, it will be understood that embodiments of the inventive subject matter are not limited to such configurations, but are intended to encompass any configuration capable of carrying out the operations described herein.

Figure 2:
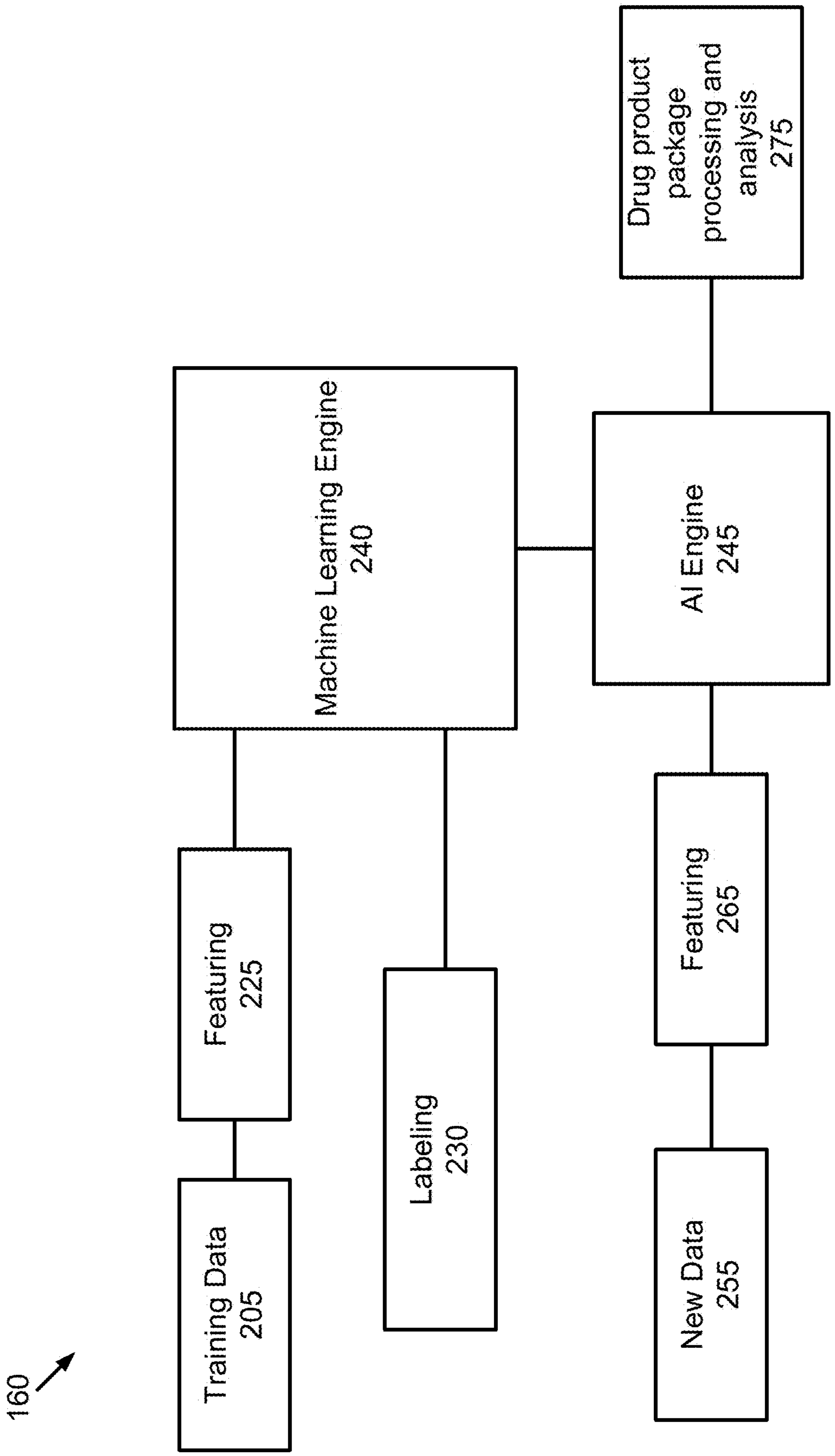
FIG. 2 is a block diagram of the AI assisted drug product package analysis system of FIG. 1 in accordance with some embodiments of the inventive concept.

As described above, the package analysis engine(s) server 155 and package analysis engine(s) module 160 may represent one or more AI systems that may be configured to generate modified images of drug product packages with labeling content removed from the surfaces thereof, to detect in a drug product package image individual ones of one or more drug products contained in the drug product package, and/or to identify these drug products that have been detected in the drug product package image. FIG. 2 is a block diagram of the package analysis engine(s) module 160 for implementing an AI system, such as a machine learning system, that can be used to detect in a drug product package image individual ones of one or more drug products contained in the drug product package, and/or to identify these drug products that have been detected in the drug product package image. The AI system of FIG. 2 may be implemented as a single AI system to detect in a drug product package image individual ones of one or more drug products contained in the drug product package, and to identify these drug products that have been detected in the drug product package image. In other embodiments, the architecture of the AI system of FIG. 2 may be duplicated to form separate AI systems to detect in a drug product package image individual ones of one or more drug products contained in the drug product package, and to identify these drug products that have been detected in the drug product package image, respectively. As shown in FIG. 2, the package analysis engine(s) module 160 may include both training modules and modules used for processing new data on which to detect and/or identify drug products in a drug product package image. The modules used in the training portion of the package analysis engine(s) module 160 include the training data module 205, the featuring module 225, the labeling module 230, and the machine learning engine 240.

The training data 205 may comprise one or more images of a drug product package that each contain one or more drug products therein. The drug product package(S) may include labeling content on a surface thereof, which may include, but is not limited to, commercial marketing information, patient identification information and/or personal healthcare information (PHI). The commercial marketing information may include, for example, a logo and/or a business name. The patient identification information may include, for example, a patient name, a patient phone number, a patient address, and/or a patient identification number. The personal health care information may include, for example, names of the one or more drug products contained in the drug product package, a time of administration for each of the one or more drug products, one or more barcodes associated with the one or more drug products, a prescription order, a patient account, an identification number, and/or other information. In some embodiments, the drug product package image may be modified, such that at least a portion of the labeling content contained on the surface thereof is removed through use of an AI system, such as a neural network, described below with reference to FIG. 3. In some embodiments, to detect in a modified drug product package image with at least a portion of the labeling content on the surface thereof removed individual ones of one or more drug products contained in the drug product package, the training data 205 may further include order information for the one or more drug products contained in the drug product package and/or an identifier for the drug product package. In further embodiments, to identify these drug products that have been detected in the drug product package image the order information included in the training data 205 may include names for the one or more drug products in the drug product package. The featuring module 225 is configured to identify the individual independent variables that are used by the package analysis engine(s) module 160 to detect and/or identify one or more drug products in, for example, a drug product package image having had the labeling content removed, which may be considered dependent variable(s). For example, the training data 205 may be generally unprocessed or formatted and include extra information in addition to drug product and/or drug product packaging information. For example, the training data 205 may include account codes, business address information, and the like, which can be filtered out by the featuring module 225. The features extracted from the training data 205 may be called attributes and the number of features may be called the dimension. The labeling module 230 may be configured to assign defined labels to the training data and to the detected and/or identified drug products to ensure a consistent naming convention for both the input features and the generated outputs. The machine learning engine 240 may process both the featured training data 205, including the labels provided by the labeling module 230, and may be configured to test numerous functions to establish a quantitative relationship between the featured and labeled input data and the generated outputs. The machine learning engine 240 may use modeling techniques to evaluate the effects of various input data features on the generated outputs. These effects may then be used to tune and refine the quantitative relationship between the featured and labeled input data and the generated outputs. The tuned and refined quantitative relationship between the featured and labeled input data generated by the machine learning engine 240 is output for use in the AI engine 245. The machine learning engine 240 may be referred to as a machine learning algorithm.

The modules used to detect in a drug product package image individual ones of one or more drug products contained in the drug product package, and/or to identify these drug products that have been detected in the drug product package image include the new data module 255, the featuring module 265, the AI engine module 245, and the drug product package processing and analysis module 275. The new data 255 may be the same data/information as the training data 205 in content and form except the new data 255 will be used for an analysis of a new drug product package rather than for training purposes. Likewise, the featuring module 265 performs the same functionality on the new data 255 as the featuring module 225 performs on the training data 205. The AI engine 245 may, in effect, be generated by the machine learning engine 240 in the form of the quantitative relationship determined between the featured and labeled input data and the output drug product package content analysis. The AI engine 245 may, in some embodiments, be referred to as an AI model. The AI engine 245 may be configured to generate modified images of a drug product package that includes indicia that distinguish between individual ones of the one or more drug products contained therein while associating the one or more drug products with order information and/or an identifier for the drug product package. The indicia may be embodied in a variety of ways including, but not limited to, boundary boxes or polygons, circles, an enclosed shape that includes straight and curved surfaces, an enclosed shape that includes only curved surfaces, and/or lines or symbols that demarcate boundaries between the one or more drug products. In some embodiments, the indicia may take a shape that approximates the shape of the drug product. The AI engine 245 may also be configured to identify one or more of the drug products based on their names. The AI engine 245 may use a variety of modeling techniques to detect in a drug product package image individual ones of one or more drug products contained in the drug product package, and to identify these drug products that have been detected in the drug product package image in accordance with different embodiments of the inventive concept including, but not limited to, a regression technique, a neural network technique, an Autoregressive Integrated Moving Average (ARIMA) technique, a deep learning technique, a linear discriminant analysis technique, a decision tree technique, a naïve Bayes technique, a K-nearest neighbors technique, a learning vector quantization technique, a support vector machine technique, and/or a bagging/random forest technique.

The drug product package processing and analysis module 275 may be configured to output the modified drug product package image with the one or more drug products identified by way of indicial, such as boundary boxes, along with names for the one or more drug products to a drug product package validation system.

Figure 3:
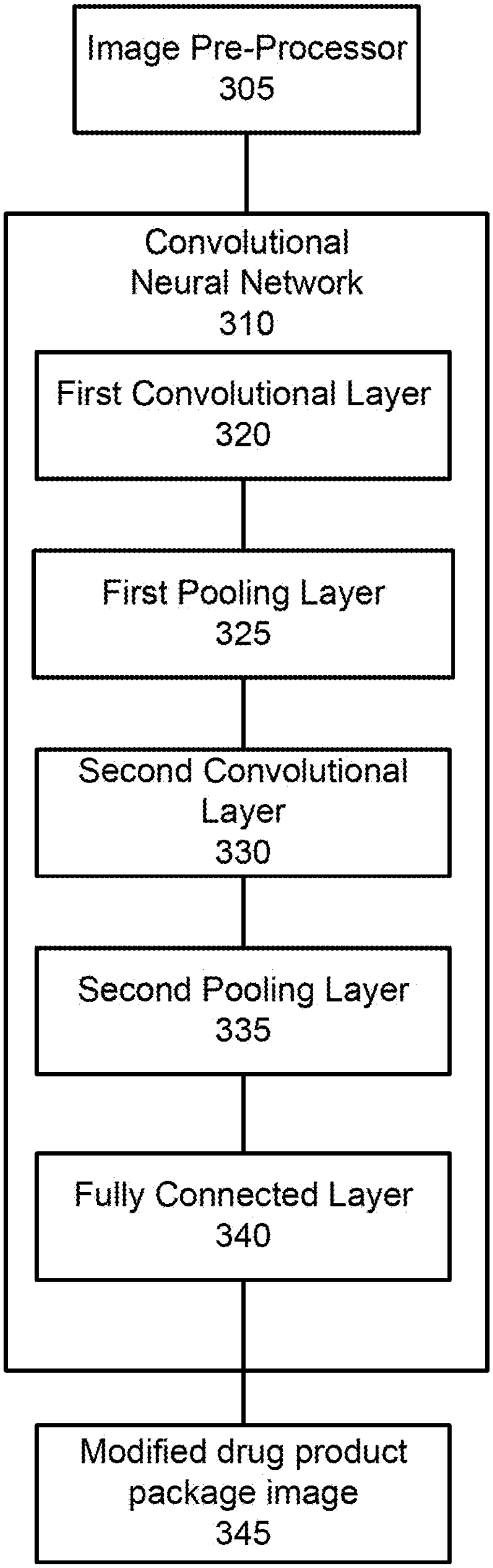
FIG. 3 is a block diagram of a convolutional neural network for detecting labeling content of the surface of a drug product package in accordance with some embodiments of the inventive concept.

As described above, the package analysis engine(s) server 155 and package analysis engine(s) module 160 may represent one or more AI systems that may be configured to generate modified images of drug product packages with labeling content removed from the surfaces thereof. FIG. 3 is a block diagram of the package analysis engine(s) module 160 for implementing an AI system, by way of a neural network, that can be used to generate modified images of drug product packages with labeling content removed from the surfaces thereof. In the example embodiment of FIG. 3, the neural network is a convolutional neural network. It will be understood, however, that the AI system for removing labeling content from a drug product package image may also be embodied as a fully connected neural network in accordance with other embodiments of the inventive concept. A convolutional neural network may, however, be useful when processing or classifying images due to the large number of pixels and the resulting large number of weights to manage in the neural network layers. A convolutional neural network may reduce the main image matrix to a matrix having a lower dimension in the first layer through convolution, which reduces the number of weights used and reduces the impact on training time.

Referring now to FIG. 3, an image pre-processor 305 may receive one or more images of a drug product package that includes labeling content displayed on the surface thereof. As will be described below with reference to FIG. 6, the image pre-processor may perform various corrections to the image data including, for example, gamma correction, noise reduction, and/or image segmentation. The pre-processed drug product package image, which may be an image represented by a matrix of dimension A×B×3, where the number 3 represents the colors red, green, and blue, may then be provided to the convolutional neural network 310. As shown in FIG. 3, the convolutional neural network 310 includes first and second convolutional layers 320 and 330 along with first and second pooling layers 325 and 335. Each of the convolutional layers 320 and 330 is a matrix of a dimension smaller than the input matrix and may be configured to perform a convolution operation with a portion of the input matrix having the same dimension. The sum of the products of the corresponding elements is the output of the convolutional layer. The output of each of the convolutional layers may also be processed through a rectified linear unit operation in which any number below 0 is converted to 0 and any positive number is left unchanged. The convolutional neural network 310 further includes first and second pooling layers 325 and 335. The pooling layers 325 and 335 may each be configured to filter the output of the convolutional layers 320 and 330, respectively, by perform a down sampling operation. The size of the pooling operation or filter is smaller than the size of the input feature map, In some embodiments, it is 2×2 pixels applied with a stride of 2 pixels. This means that the pooling layer will always reduce the size of each feature map by a factor of 2, e.g. each dimension is halved, reducing the number of pixels or values in each feature map to one quarter the size. For example, a pooling layer applied to a feature map of 6×6 (36 pixels) will result in an output pooled feature map of 3×3 (9 pixels). The final output layer is a normal fully-connected neural network layer 340, which gives the output as modified drug product package image 345 with at least a portion of the labeling content on a surface thereof removed.

Figure 4:
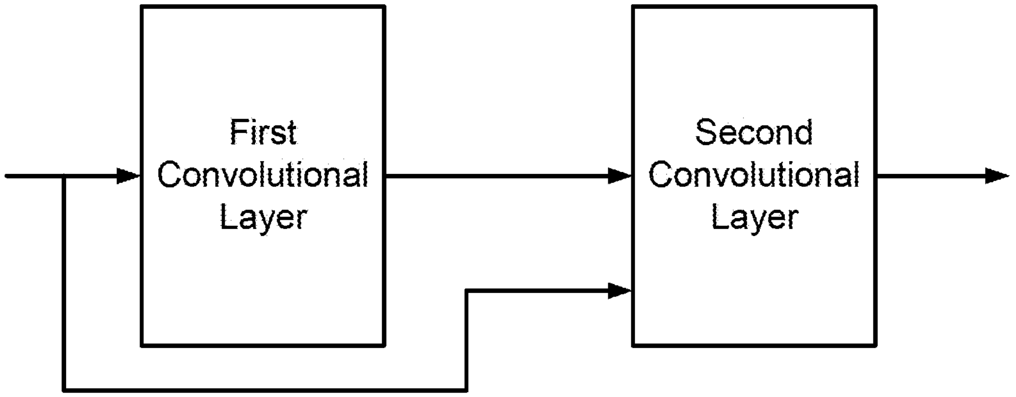
FIG. 4 is a block diagram of a skip connection arrangement between convolutional layers of the convolutional neural network of FIG. 3 in accordance with some embodiments of the inventive concept.

In some embodiments of the inventive concept, the convolutional neural network 310 may be a residual neural network in which skip connections are used between the convolutional layers 320 and 330. An example of the skip connection is shown in FIG. 4. Specifically, in a skip connection a convolutional neural network involves a convolutional layer receiving as an input both the output of a previous convolutional layer and the input to the previous convolutional layer.

It will be understood that while two convolutional layers 320 and 330 are shown in in the example convolutional neural network 310 of FIG. 3 for purposes of illustration, a convolutional neural network according to various embodiments of the inventive concept may contain numerous convolutional layers and may exceed 100 layers in some embodiments.

Figure 5:
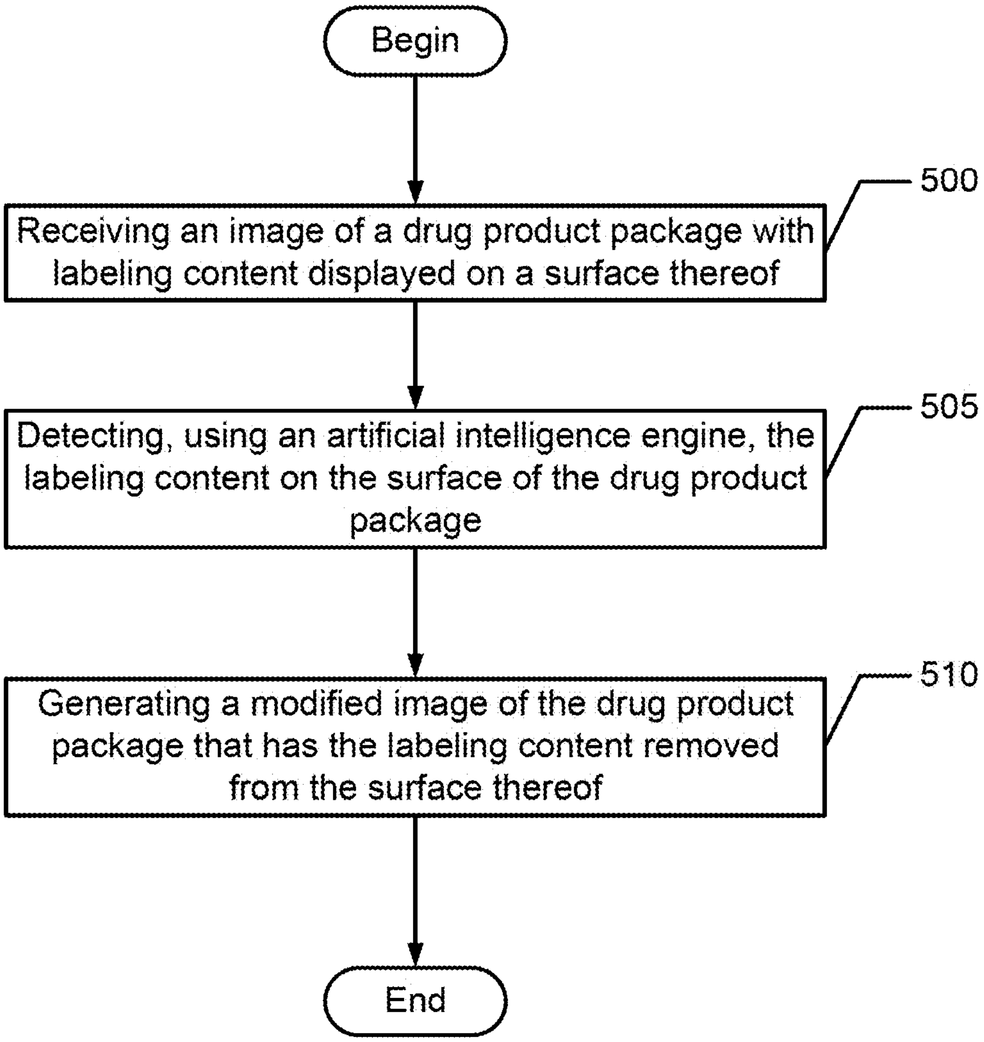
FIG. 5 is a flowchart that illustrates operations for performing drug product package analysis in accordance with some embodiments of the inventive concept.

FIGS. 3 and 7-10 are flowcharts that illustrate operations for performing drug product package analysis including removal of labeling content therefrom to facilitate validations of the contents therein in accordance with some embodiments of the inventive concept. Referring now to FIG. 5, operations begin at block 500 where the convolutional neural network 310 receives an image of a drug product package with labeling content displayed on a surface thereof. The labeling content may include, but is not limited to, commercial marketing information, patient identification information and/or personal healthcare information (PHI). The commercial marketing information may include, for example, a logo and/or a business name. The patient identification information may include, for example, a patient name, a patient phone number, a patient address, and/or a patient identification number. The personal health care information may include, for example, names of the one or more drug products contained in the drug product package, a prescribed time of administration for each of the one or more drug products, one or more barcodes associated with the one or more drug products, a prescription order, a patient account, an identification number, and/or other information. At block 505, the labeling content on the surface of the drug product package may be detected using the convolutional neural network 310. The convolutional neural network 310 may then generate a modified image of the drug product package that has the labeling content removed from the surface thereof at block 510.

Figure 6:
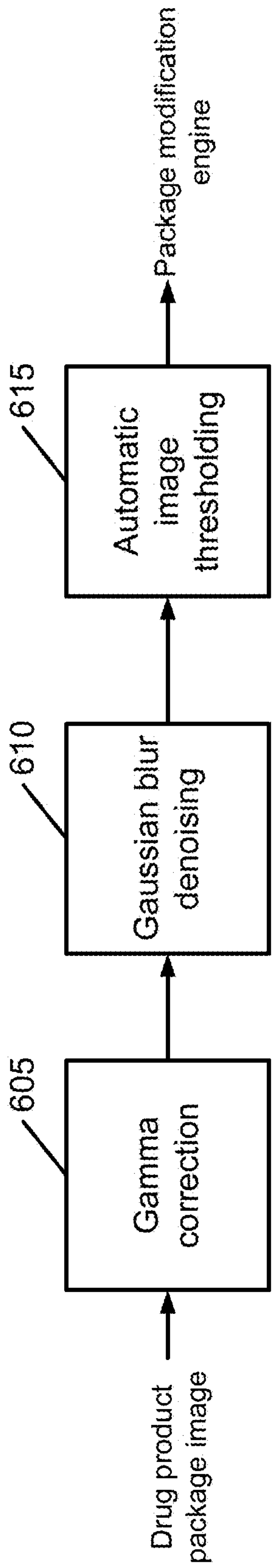
FIG. 6 is a block diagram that illustrates drug product package image pre-processing in accordance with some embodiments of the inventive concept.
Figure 7:
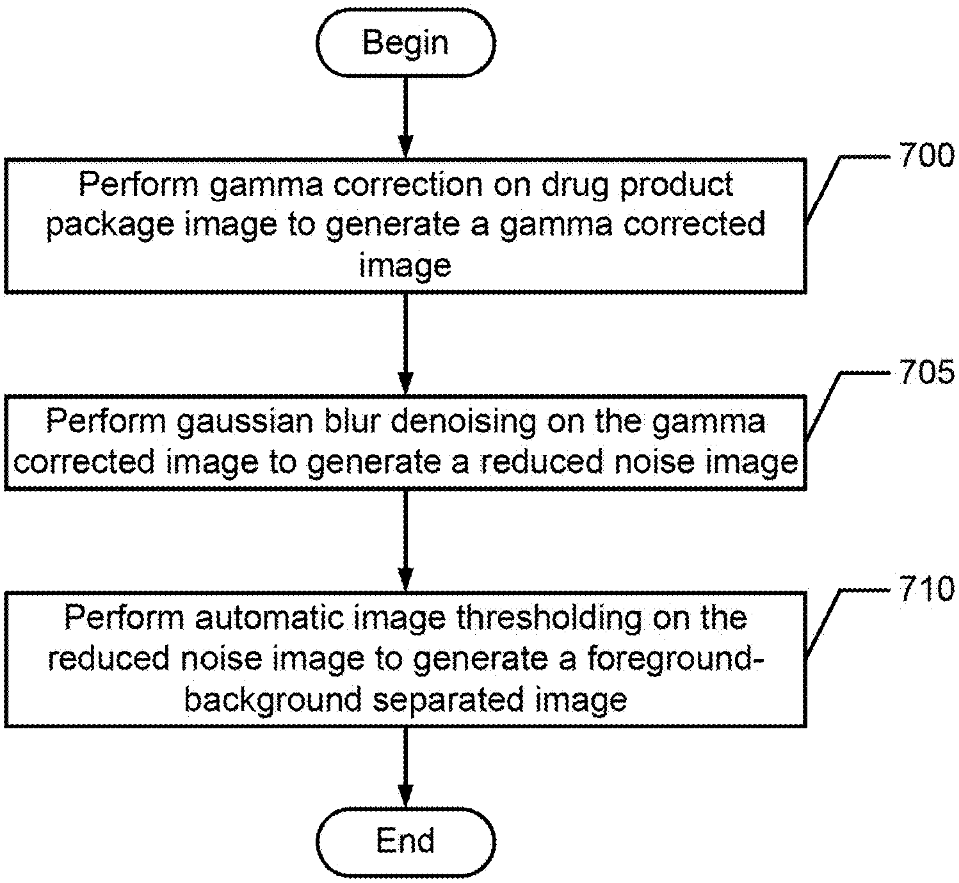
FIGS. 7-10 are flowcharts that illustrate further operations for performing drug product package analysis in accordance with some embodiments of the inventive concept.

As described above, the drug product package image may undergo pre-processing to perform various corrections to the image data. Referring now to FIGS. 6 and 7, the operations begin at block 700 where a gamma correction module 605 performs gamma correction on the drug product package image to generate a gamma corrected image. One or more cameras may make an image darker; the gamma correction may brighten the image to allow the convolutional neural network 310 to better recognize the edges of various elements displayed in the image. Gamma correction may be embodied as a power law transform, except for low luminosities where it may be linear to avoid having an infinite derivative at luminance zero. This is the traditional nonlinearity applied for encoding SDR images. The exponent or "gamma," may have a value of 0.45, but the linear portion of the lower part of the curve may make the final gamma correction function to be closer to a power low exponent of 0.5, i.e., a square root transform; therefore, the gamma correction may comply with the DeVries-Rose law of brightness perception. At block 705, the gaussian blur denoising module 610 is used to perform gaussian blur denoising on the gamma corrected image to generate a reduced noise image. The gaussian blur denoising module or filter 610 may be a linear filter. It may be used to blur the image and/or to reduce the noise. Two gaussian blur denoising filters 610 may be used such that the outputs are subtracted for "unsharp masking" (edge detection). The gaussian blur denoising module or filter 610 may blur edges and reduce contrast. The Median filter is a non-linear filter that may be used as a way to reduce noise in an image. At block 710, the automatic image thresholding module 615 may perform automatic image thresholding on the reduced noise image to generate a foreground-background separated image. Thresholding is a technique used in image segmentation applications. Thresholding involves the selection of a desired gray-level threshold value for separating objects of interest in an image from the background based on their gray-level distribution. The Otsu method is a type of global thresholding that depends only on the gray value of the image. The Otsu method is a global thresholding selection method, which involves computing a gray level histogram. When applied in only one dimension an image may not be sufficiently segmented. A two-dimensional Otsu method may be used that is based on both the gray-level threshold of each pixel as well as its spatial correlation information with the neighborhood surrounding the pixel. As a result, the Otsu method may provide satisfactory segmentation when applied to noisy images. The output image from the pre-processing modules of FIG. 6 may be applied to a drug product package modification engine, such as the convolutional neural network 310 of FIG. 3.

Figure 8:
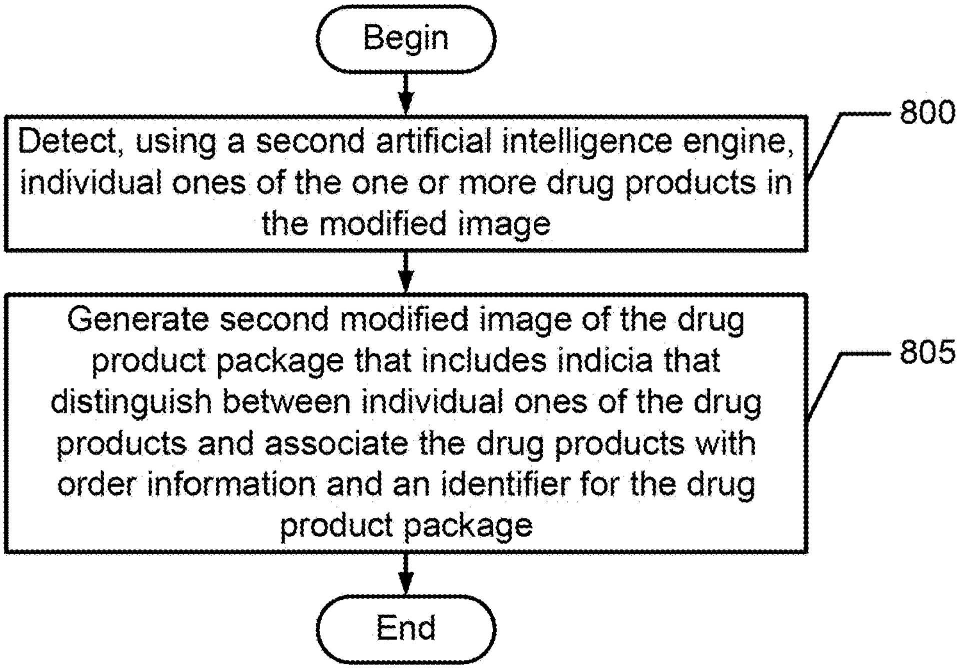
Figure 13:
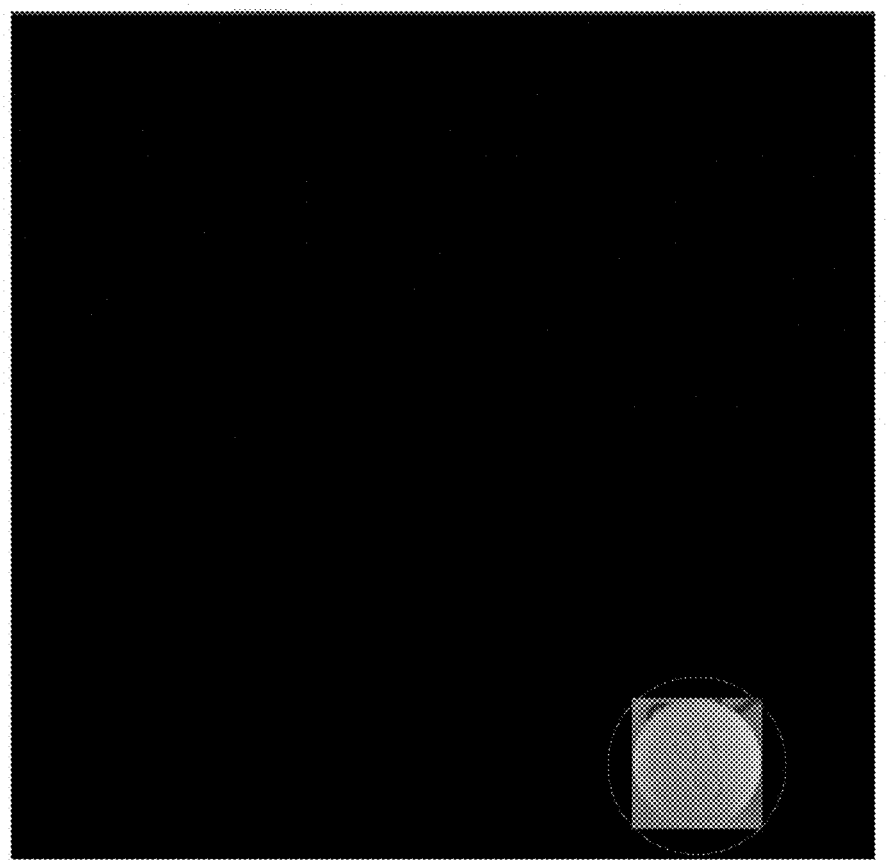
FIGS. 13 and 14 are diagrams that illustrate indicia that distinguish between individual drug products in a drug product package image in accordance with some embodiments of the inventive concept.

Referring now to FIG. 8, the drug product package image may be further processed to facilitate validation of the contents therein by detecting, at block 800, individual ones of the one or more drug products in the modified image having the labeling content removed from the surface thereof. The detection may be carried out using an AI engine, such as the AI engine 245 described above with respect to FIG. 2 based on the modified drug product package image with the labeling content removed from the surface thereof along with order information for the one or more drug products contained in the drug product package and/or an identifier for the drug product package. The AI engine may generate a second modified image of the drug product package that includes indicia that distinguish between individual ones of the drug products and associate the drug products with order information and an identifier for the drug product package at block 805. In some embodiments, bounding boxes may be used as indicia that distinguish between individual ones of the drug products as shown, for example, in FIG. 13, which illustrates the use of a circle as an indicia to identify the location of a particular drug product.

Figure 9:
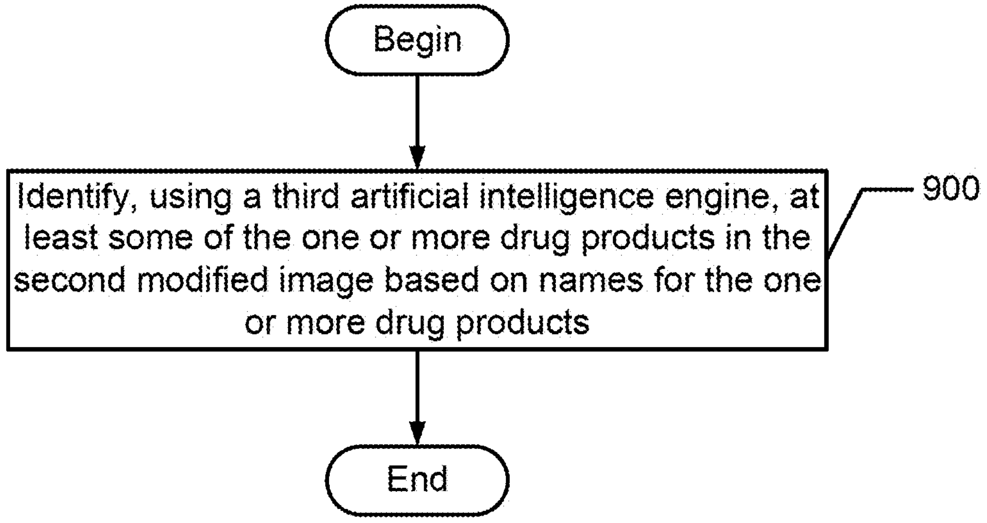
Figure 14:
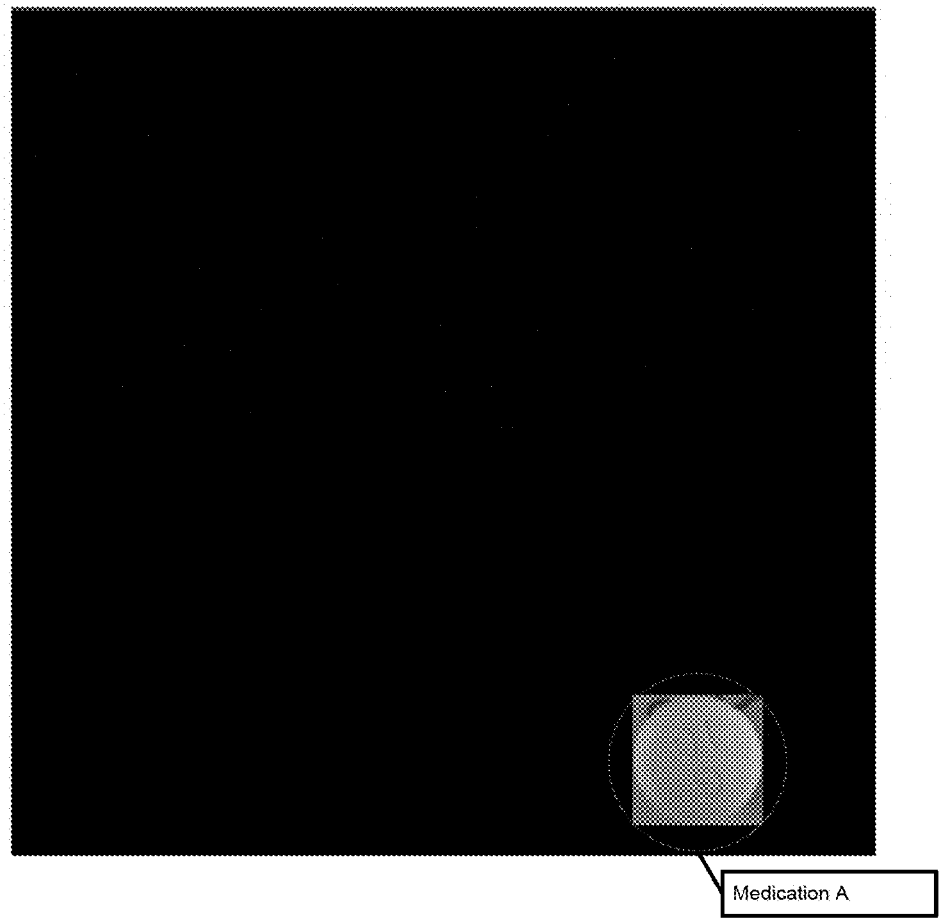

Referring now to FIG. 9, the drug product package image may be further processed to facilitate validation of the contents therein by identifying, at block 900, at least some of the one or more drug products in the second modified image having the individual ones of the drug products detected, based on names for the one or more drug products. The identification may be carried out using an AI engine, such as the AI engine 245 described above with respect to FIG. 2 based on the modified drug product package image with the individual ones of the one or more drug products detected and order information, which includes names for the one or more drug products in the drug product package. In accordance with some embodiments of the inventive concept, the names may be associated with drug product attributes in a reference database. These attributes may include, but are not limited to, drug product shape, color, etching(s), imprint(s), weight, and/or label(s). FIG. 14 illustrates the drug product of FIG. 13 that has been annotated with the name "Medication A." In some embodiments, the identified one or more drug products may include a fragmented drug product, such as a portion of a pill or tablet. The identified one or more drug products may further include the identification of debris, resulting from damage to a drug product that reduces all or a portion of the drug product to powder, for example. The identification of the one or more drug products in the drug product package image by name along with identifying portions of drug products and package debris may facilitate generating a count of the drug products in the drug product package for use in validating the contents of the drug product package. The drug product package image may be annotated with the names determined for the one or more drug products, but there may be circumstances where the AI engine is unable to determine a name for one or more of the drug products in the drug product package image. If there is only one or a few drug products for which a name was unable to be determined, then these drug products may be annotated with a temporary name or National Drug Code (NDC) that is new or not seen previously. In some embodiments, further operations may be performed to determine the names of these drug products, such as those described hereafter with reference to FIG. 10.

Figure 10:
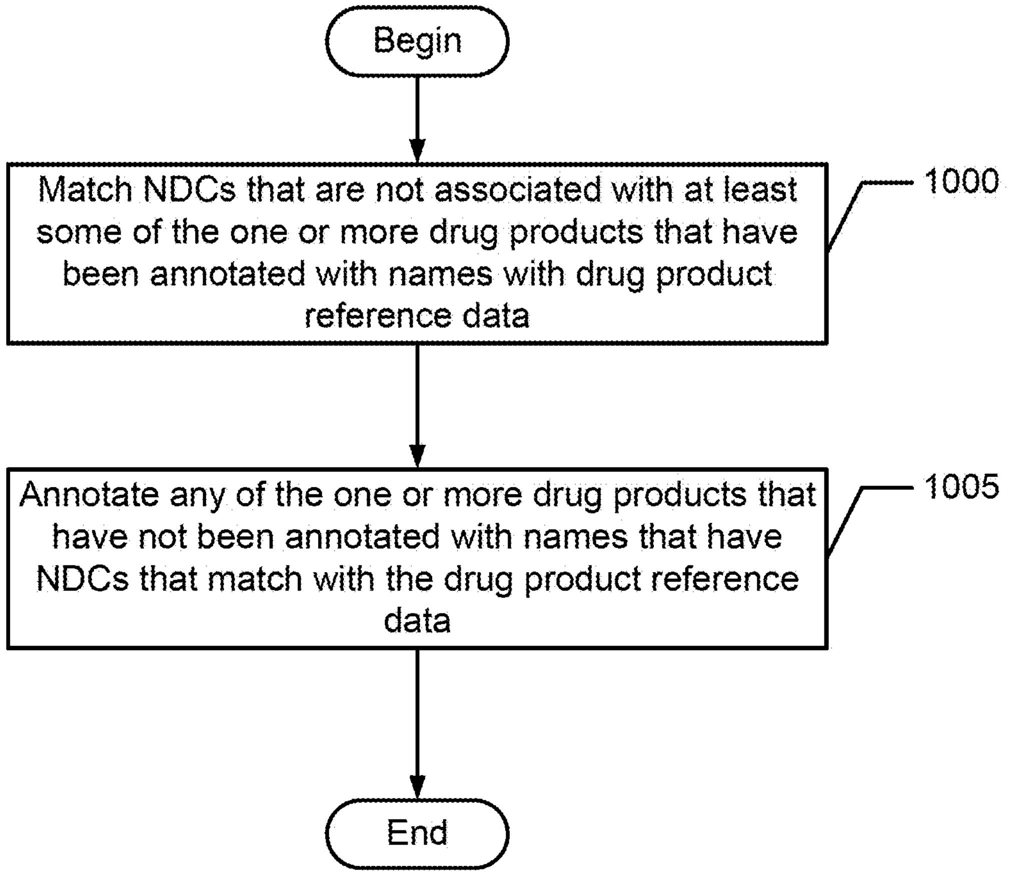

Referring now to FIG. 10, operations for determining the names of drug products that were not identified by name using the AI system operations of FIG. 9 begin at block 1000 where a matching operation is performed between National Drug Codes (NDCs) that are included in the order information, but are not associated with any of the named drug products and drug product reference data, e.g., drug product shape, color, etching(s), and/or label(s) information. A determination may then be made at block 1005 whether any of the un-named drug products in the drug product package image match the shape, color, etching(s), imprint(s), weight, and/or label(s) information associated with an NDC included in the order. If there is a match, the un-name drug product may be assigned a name corresponding to the associated NDC.

Figure 11:
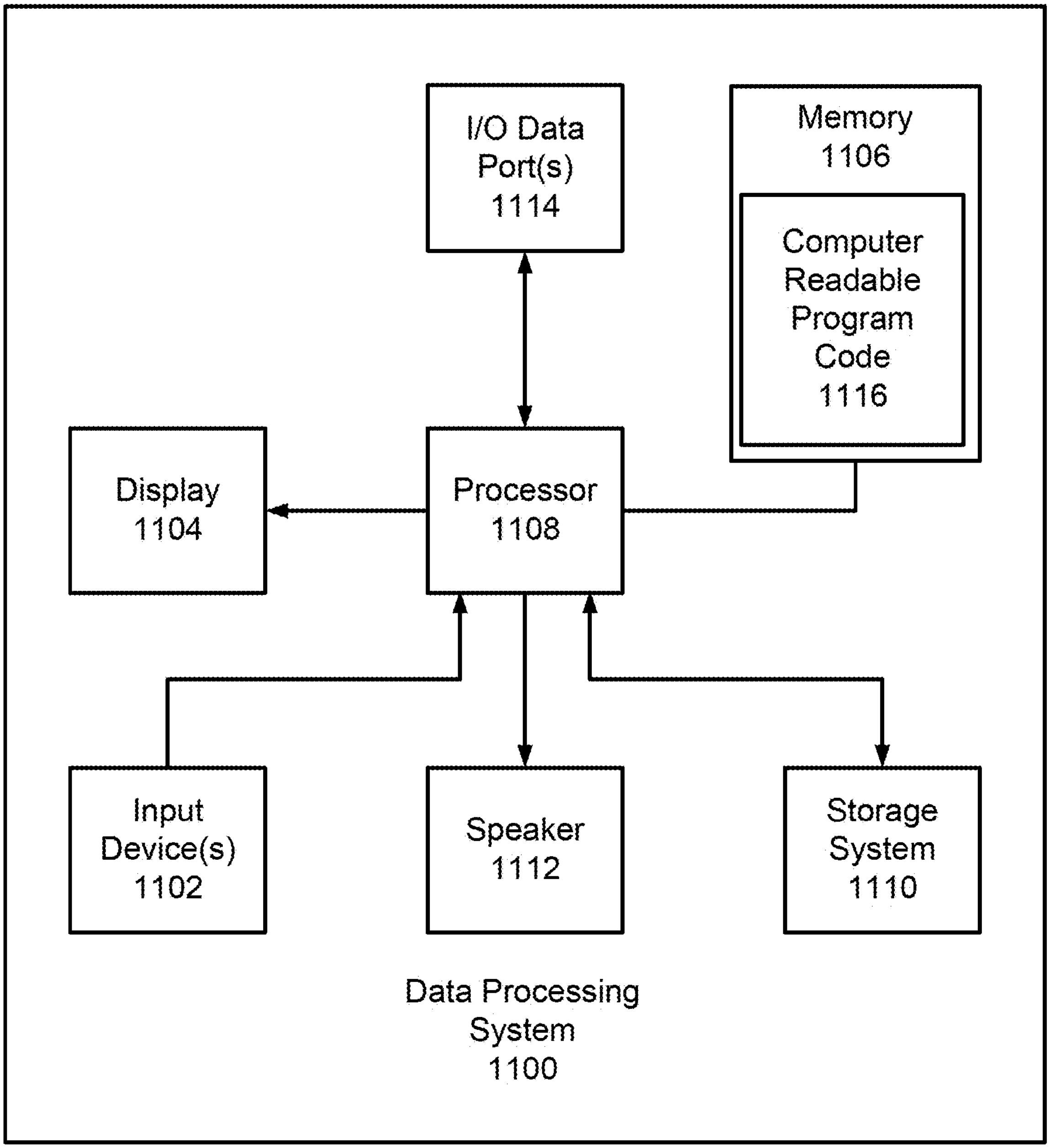
FIG. 11 is a data processing system that may be used to implement one or more servers in the AI assisted drug product package analysis system of FIG. 1 in accordance with some embodiments of the inventive concept.

Referring now to FIG. 11, a data processing system 1100 that may be used to implement the drug product package image analysis engine(s) server 155 of FIG. 1, in accordance with some embodiments of the inventive concept, comprises input device(s) 1102, such as a keyboard or keypad, a barcode scanner, or RFID reader, a display 1104, and a memory 1106 that communicates with a processor 1108. The data processing system 1100 may further include a storage system 1110, a speaker 1112, and an input/output (I/O) data port(s) 1114 that also communicate with the processor 1108. The processor 1108 may be, for example, a commercially available or custom microprocessor. The storage system 1110 may include removable and/or fixed media, such as floppy disks, ZIP drives, hard disks, or the like, as well as virtual storage, such as a RAMDISK. The I/O data port(s) 1114 may be used to transfer information between the data processing system 1100 and another computer system or a network (e.g., the Internet). These components may be conventional components, such as those used in many conventional computing devices, and their functionality, with respect to conventional operations, is generally known to those skilled in the art. The memory 1106 may be configured with computer readable program code 1116 to facilitate AI assisted removal of extraneous labeling content from a surface of a drug product package and/or detection and identification of the one or more drug products contained therein to validate the drug product package contents according to some embodiments of the inventive concept.

Figure 12:
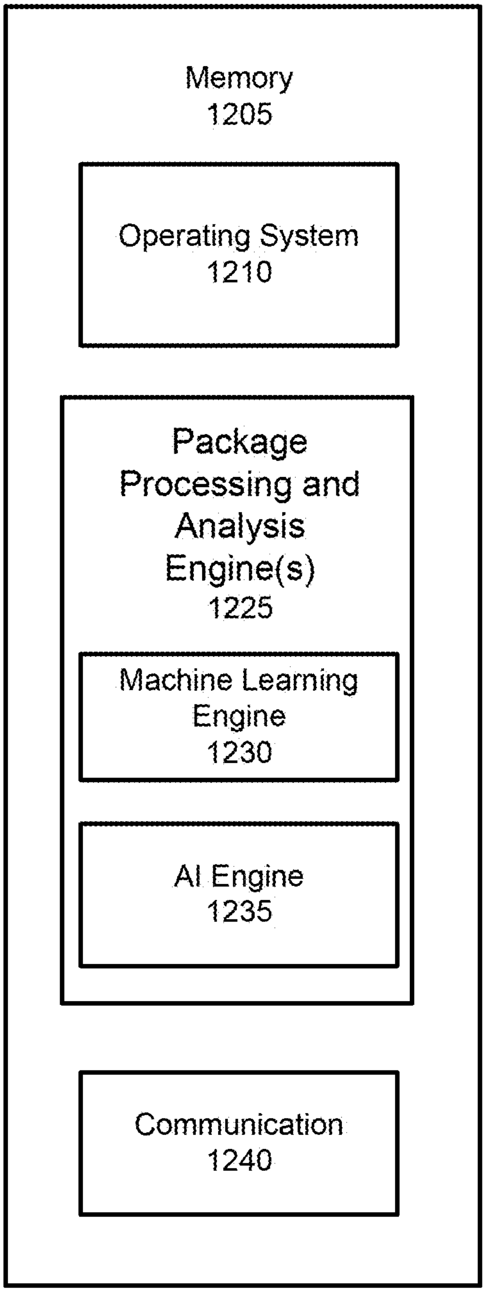
FIG. 12 is a block diagram that illustrates a software/hardware architecture for use in the AI assisted drug product package analysis system of FIG. 1 in accordance with some embodiments of the inventive concept.

FIG. 12 illustrates a memory 1205 that may be used in embodiments of data processing systems, such as the drug product package analysis engine(s) server 155 of FIG. 1 and the data processing system 1100 of FIG. 11, respectively, to facilitate AI assisted removal of extraneous labeling content from a surface of a drug product package and/or detection and identification of the one or more drug products contained therein to validate the drug product package contents according to some embodiments of the inventive concept. The memory 1205 is representative of the one or more memory devices containing the software and data used for facilitating operations of the drug product package analysis engine(s) server 155 and the drug product package analysis engine(s) module 160 as described herein. The memory 1205 may include, but is not limited to, the following types of devices: cache, ROM, PROM, EPROM, EEPROM, flash, SRAM, and DRAM. As shown in FIG. 12, the memory 1205 may contain five or more categories of software and/or data: an operating system 1210, a drug product package processing and analysis engine(s) module 1225, and a communication module 1240. In particular, the operating system 1210 may manage the data processing system's software and/or hardware resources and may coordinate execution of programs by the processor. The drug product package processing and analysis engine(s) module 112 may comprise a machine learning engine module 1230 and an AI engine module 1235. The machine learning engine module 1230 may be configured to perform one or more operations described above with respect to the machine learning engine 240, the convolutional neural network 310, and the flowcharts of FIGS. 5 and 7-10. The AI engine module 1225 may be configured to perform one or more operations described above with respect to the AI engine 245, the convolutional neural network 310, and the flowcharts of FIGS. 5 and 7-10. The communication module 1240 may be configured to support communication between, for example, the drug product package analysis engine(s) server 155 and, for example, a drug product package validation system.

Although FIGS. 11-12 illustrate hardware/software architectures that may be used in data processing systems, such as the drug product package analysis engine(s) server 155 of FIG. 1 and the data processing system 1100 of FIG. 11, respectively, in accordance with some embodiments of the inventive concept, it will be understood that embodiments of the present invention are not limited to such a configuration but are intended to encompass any configuration capable of carrying out operations described herein.

Computer program code for carrying out operations of data processing systems discussed above with respect to FIGS. 1-11, 13, and 14 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the drug product package analysis engine(s) server 155 of FIG. 1 and the data processing system 1100 of FIG. 11 may each be implemented as a single processor system, a multi-processor system, a multi-core processor system, or even a network of standalone computer systems, in accordance with various embodiments of the inventive concept. Each of these processor/computer systems may be referred to as a "processor" or "data processing system."

The data processing apparatus described herein with respect to FIGS. 1-13 may be used to facilitate AI assisted removal of extraneous labeling content from a surface of a drug product package and/or detection and identification of the one or more drug products contained therein to validate the drug product package contents according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 1205 when coupled to a processor includes computer readable program code that, when executed by the processor, causes the processor to perform operations including one or more of the operations described herein with respect to FIGS. 1-10, 13, and 14.

As described above, embodiments of the inventive concept may provide an AI assisted drug product package analysis system that may use AI technology, such as a convolutional neural network to detect the labeling content on the surface of a drug product package to generate a modified image of the drug product package with the labeling content removed and one or more machine learning engines to detect and identify the drug products contained in the drug product package. this may improve the accuracy of the package validation process before, for example, a pharmacy or medical center releases packaged drug products to a customer or patient.

Further Definitions and Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises," "comprising," "include", "including", "includes", "have", "has", "having", or variants thereof when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

It will also be understood that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method comprising:

receiving an image of a drug product package that contains one or more drug products therein, the image including labeling content displayed on a surface thereof;

detecting, using an artificial intelligence engine, the labeling content on the surface of the drug product package; and generating a modified image of the drug product package that has the labeling content removed from the surface thereof.

2. The method of claim 1, wherein the labeling content comprises commercial marketing information, patient identification information, or personal healthcare information.

3. The method of claim 2, wherein the commercial marketing information comprises a logo or a business name;

wherein the patient identification information comprises a patient name, a patient phone number, a patient address, or a patient identification number; and wherein the personal healthcare information comprises names of the one or more drug products, a number of each of the one or more drug products, a prescribed time of administration for each of the one or more drug products, one or more barcodes associated with the one or more drug products, a prescription order, a patient account, or an identification number.

4. The method of claim 1, further comprising:

performing gamma correction on the image of the drug product package responsive to receiving the image of the drug product package to generate a gamma corrected image of the drug product package;

performing gaussian blur denoising on the gamma corrected image of the drug product package to generate a reduced noise image of the drug product package; and performing automatic image thresholding on the reduced noise image of the drug product package to generate a foreground-background separated image of the drug product package;

wherein detecting, using the artificial intelligence engine, the labeling content comprises:

detecting, using the artificial intelligence engine, the labeling content on the surface of the foreground-background separated image of the drug product package.

5. The method of claim 4, wherein the artificial intelligence engine is a convolutional neural network.

6. The method of claim 5, wherein the convolutional neural network comprises a plurality of convolutional layers with at least some of the plurality of convolutional layers being connected to one another via a skip connection.

7. The method of claim 1, wherein the artificial intelligence engine is a first artificial intelligence engine and the modified image is a first modified image, the method further comprising:

receiving order information for the one or more drug products and an identifier for the drug product package;

detecting, using a second artificial intelligence engine, individual ones of the one or more drug products in the first modified image; and generating a second modified image of the drug product package that includes indicia that distinguish between the individual ones of the one or more drug products and associate the one or more drug products with the order information and the identifier for the drug product package.

8. The method of claim 7, wherein the indicia that distinguish between the individual ones of the one or more drug products comprise one or more bounding boxes.

9. The method of claim 7, wherein the order information comprises names for the one or more drug products in the drug product package, the method further comprising:

identifying, using a third artificial intelligence engine, at least some of the one or more drug products in the second modified image based on the names for the one or more drug products;

wherein the names are associated with drug product attributes in a reference database.

10. The method of claim 9, wherein the at least some of the one or more drug products includes a fragmented one of the one or more drug products.

11. The method of claim 9, wherein the method further comprises:

identifying, using the third artificial intelligence engine, a portion of the one or more drug products as debris resulting from damage to the one or more drug products.

12. The method of claim 9, further comprising:

annotating the at least some of the one or more drug products in the second modified image with the names for the one or more drug products.

13. The method of claim 12, further comprising:

annotating any of the one or more drug products that have not been annotated with the names with a temporary name.

14. The method of claim 12, wherein the names are first names and the order information comprises National Drug Codes (NDCs) for the one or more drug products in the drug product package, the method further comprising:

matching NDCs that are not associated with the at least some of the one or more drug products that have been annotated with the first names with drug product reference data; and annotating any of the one or more drug products that have not been annotated with the names that have associated NDCs that match with the drug product reference data with second names based on drug product reference data.

15. The method of claim 14, wherein the drug product reference data comprise a drug product shape, a drug product color, a drug product etching, drug product imprint, a drug product weight, and/or a drug product label.

16. A system, comprising:

a processor; and a non-transitory memory coupled to the processor and comprising computer readable program code embodied in the non-transitory memory that is executable by the processor to perform operations comprising:

receiving an image of a drug product package that contains one or more drug products therein, the image including labeling content displayed on a surface thereof;

detecting, using an artificial intelligence engine, the labeling content on the surface of the drug product package; and generating a modified image of the drug product package that has the labeling content removed from surface thereof.

17. The system of claim 16, wherein the operations further comprise:

performing gamma correction on the image of the drug product package responsive to receiving the image of the drug product package to generate a gamma corrected image of the drug product package;

performing gaussian blur denoising on the gamma corrected image of the drug product package to generate a reduced noise image of the drug product package; and performing automatic image thresholding on the reduced noise image of the drug product package to generate a foreground-background separated image of the drug product package;

wherein detecting, using the artificial intelligence engine, the labeling content comprises:

detecting, using the artificial intelligence engine, the labeling content on the surface of the foreground-background separated image of the drug product package.

18. The system of claim 17, wherein the artificial intelligence engine is a convolutional neural network.

19. A non-transitory computer program product, comprising:

a non-transitory computer readable storage medium comprising computer readable program code embodied in the medium that is executable by a processor to perform operations comprising:

receiving an image of a drug product package that contains one or more drug products therein, the image including labeling content displayed on a surface thereof;

detecting, using an artificial intelligence engine, the labeling content on the surface of the drug product package; and generating a modified image of the drug product package that has the labeling content removed from surface thereof.

20. The non-transitory computer program product of claim 19, wherein the operations further comprise:

performing gamma correction on the image of the drug product package responsive to receiving the image of the drug product package to generate a gamma corrected image of the drug product package;

performing gaussian blur denoising on the gamma corrected image of the drug product package to generate a reduced noise image of the drug product package; and performing automatic image thresholding on the reduced noise image of the drug product package to generate a foreground-background separated image of the drug product package;

wherein detecting, using the artificial intelligence engine, the labeling content comprises:

detecting, using the artificial intelligence engine, the labeling content on the surface of the foreground-background separated image of the drug product package.

* * * * *